United States Patent [19]

Schulman et al.

[11] 4,112,926
[45] Sep. 12, 1978

[54] METHOD AND APPARATUS FOR MEASURING AND TREATING HYPERACTIVITY IN HUMAN BEINGS

[75] Inventors: Jerome L. Schulman, Chicago; Jay Kaplan, Buffalo Grove, both of Ill.

[73] Assignee: The Children's Memorial Hospital, Chicago, Ill.

[21] Appl. No.: 748,518

[22] Filed: Dec. 8, 1976

[51] Int. Cl.$^2$ ............................................. A61B 5/10
[52] U.S. Cl. .................... 128/2 S; 128/2 N; 35/22 R; 235/92 PL; 340/573
[58] Field of Search .......... 128/2 S, 2 N, 2 R, 2.05 P, 128/2.05 T, 2.06 A; 35/22 R; 235/92 PL; 340/279

[56] References Cited

U.S. PATENT DOCUMENTS

| | | | |
|---|---|---|---|
| 3,267,934 | 8/1966 | Thornton | 128/2.06 A |
| 3,439,358 | 4/1969 | Salmons | 128/2 S |
| 3,593,705 | 7/1971 | Thomas et al. | 128/2.06 A |
| 3,802,417 | 4/1974 | Lang | 128/2 R |
| 3,854,472 | 12/1974 | Giroi et al. | 128/2.06 A |
| 3,929,335 | 12/1975 | Malick | 340/279 X |
| 4,033,332 | 7/1977 | Hardway, Jr. et al. | 128/2 S |
| 4,038,525 | 7/1977 | Freeman | 235/92 PL X |

FOREIGN PATENT DOCUMENTS

| | | | |
|---|---|---|---|
| 1,383,594 | 2/1975 | United Kingdom | 128/2 S |
| 302,103 | 6/1971 | U.S.S.R. | 128/2 S |

OTHER PUBLICATIONS

Colburn et al., "An Ambulatory Activity Monitor...", ISA Trans., vol. 15, No. 2, pp. 149-154, May 5, 1976.
Polhemus et al., "A Rocking Motion Sensor...", ISA Trans., vol. 15, No. 2, pp. 192-196, May 5, 1976.
McPartland et al., "Instrumentation & Techniques...", Behavior Research Methods & Inst., 1976, vol. C (4), 357-360.
McPartland et al., "Activity Sensors... Evaluation", IEEE Trans. on Bio Med. Eng., Mar. 1976, pp. 175-178.

*Primary Examiner*—Lee S. Cohen
*Attorney, Agent, or Firm*—McDougall, Hersh & Scott

[57] ABSTRACT

A method of measuring hyperactivity includes determining the total number of movements of the subject as well as the number of movements which occur at a rate exceeding a preselected threshold. When the rate exceeds the threshold, biofeedback conditioning may be employed to alert the patient in order to condition him against such activity. An apparatus employing the method includes a counting unit worn on the belt of the subject. The counting unit records movement detected by a set of mercury switches. The total number of times a mercury switch is opened is counted as well as the number of times the rate threshold is exceeded. This information is stored in the counters for subsequent evaluation. An oscillator circuit gated by the counting unit provides an audible signal to the subject when the rate threshold is exceeded. A readout and display circuit is utilized for obtaining the information stored in the counting unit.

14 Claims, 3 Drawing Figures

METHOD AND APPARATUS FOR MEASURING AND TREATING HYPERACTIVITY IN HUMAN BEINGS

BACKGROUND OF THE INVENTION

The present invention relates to the detection and treatment of hyperactivity. More specifically, it relates to methods and devices for detecting the extent of hyperactivity of a subject.

Several reports indicate that hyperactivity is the most common reason for referral in the practice of child psychiatry. The list of possible etiologies is quite extensive but would certainly include acting out behavior as a consequence of emotional disturbance, direct manifestation of intrapsychic anxiety, emotional reaction to physical disabilities, boredom, maturational delay, cerebral dysfunction, cerebral damage, and metabolic dysfunction. The most prominant management approaches for the treatment of hyperactivity has been pharmacotherapy and behavior therapy. It is estimated that 200,000 children in the U.S. are currently receiving amphetamines for the purpose of controlling hyperactive behavior. Despite the widespread use of psychoactive medication with children, the efficacy and wisdom of the present application of pharmacotherapy remains open to question.

In the past decade there has been an increasing application of various behavior modification procedures in the control of hyperactive behavior. A growing number of investigators report considerable success with the application of behavioral strategies to hyperactivity. It is impossible to assess the effectiveness of such treatment, however, without reliable pre and post measures of activity level. The prior art includes several categories of devices for such measurements including devices for sedentary measurement, experimental room designs, devices for measurement of free ranging movement and observational techniques.

Sedentary measuring devices include mechanical devices which allow the experimenter to record activity level of a subject restricted to movement on a particular instrument, usually a platform or chair-like apparatus. Such devices have considerable sensitivity and good reliability. These devices are, however, costly and there is a lack of convincing evidence concerning the extent to which activity level measured over short intervals under sedentary conditions generalizes to other settings.

Experimental room designs provide greater flexibility than sedentary devices. These designs generally involve use of an experimental chamber with a chair fastened to the center of the floor. An ultrasonic motion detector is provided in the chamber so that the subject's movement, including arm, leg, and general body activity, is detected. An inherent disadvantage of this technique involves the necessity for an observer with some expertise in rating or operating the apparatus. Again, as with the sedentary devices, measurement of activity in a small room may not relate to findings under more normal conditions.

Until recently there have been relatively few instruments which may be attached directly to the subject's body permitting free field monitoring. An example of such a device is the Actometer, a modified calendar wristwatch in which movement is effective for winding the device. See the "American Journal of Mental Deficiency", Volume 64, 1959, pages 455–56. Even though the Actometer appears to be a useful measuring device, it has several shortcomings including an unequal sensitivity to different types of movement.

There has been a need for a small yet highly accurate unit which can be worn by the subject in his daily routine. Such a device, according to the present invention, is capable of both measuring the activity level of the subject as well as providing biofeedback to advise the subject when his activity rate exceeds a preselected threshold.

It is accordingly an object of the present invention to provide a method and apparatus for providing a reliable and valid measure of activity level.

It is another object of the invention to provide an instrument capable of measuring activity level in the normal environment of the subject.

Another object of the invention is to provide an activity measuring instrument with biofeedback enabling the subject to be alerted to excesses in his activity level.

Other objects and advantages of the invention will be apparent from the remaining portion of the specification.

DETAILED DESCRIPTION

Figure 1:
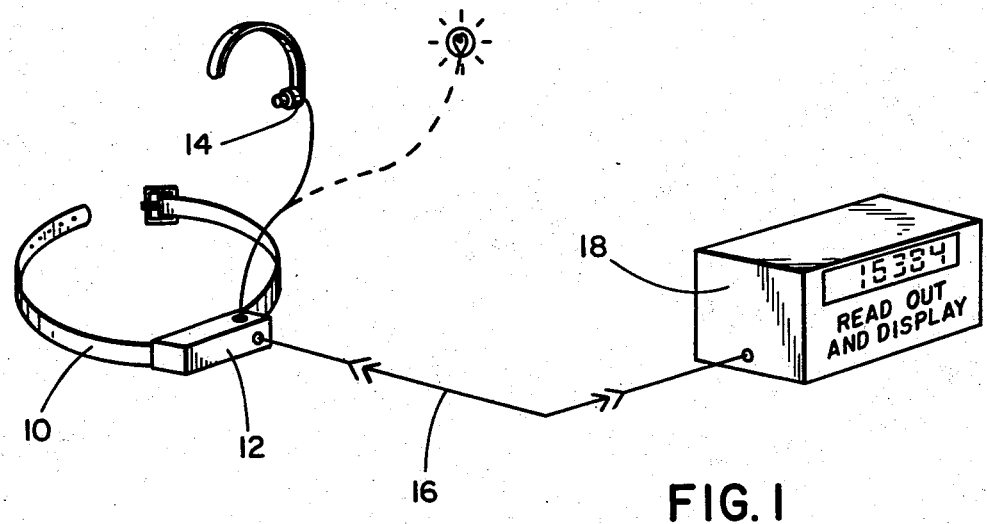
FIG. 1 is a view of the apparatus according to the invention illustrating the activity unit worn by the subject, the readout and display device.

Referring to FIG. 1, the subject whose activity is to be monitored attaches the activity counting unit 12 to a belt 10 worn about his waist. The activity unit 12 optionally has connected thereto an earphone 14 worn by the subject to provide a biofeedback signal to be described.

As indicated by the dashed lines, it is possible to provide other types of biofeedback as, for example, a visual indication. Such an option might be used where the patient is deaf or otherwise unresponsive to an audio signal. Similarly, other types of biofeedback devices could be employed utilizing other senses of the subject, such as touch.

Figure 2:
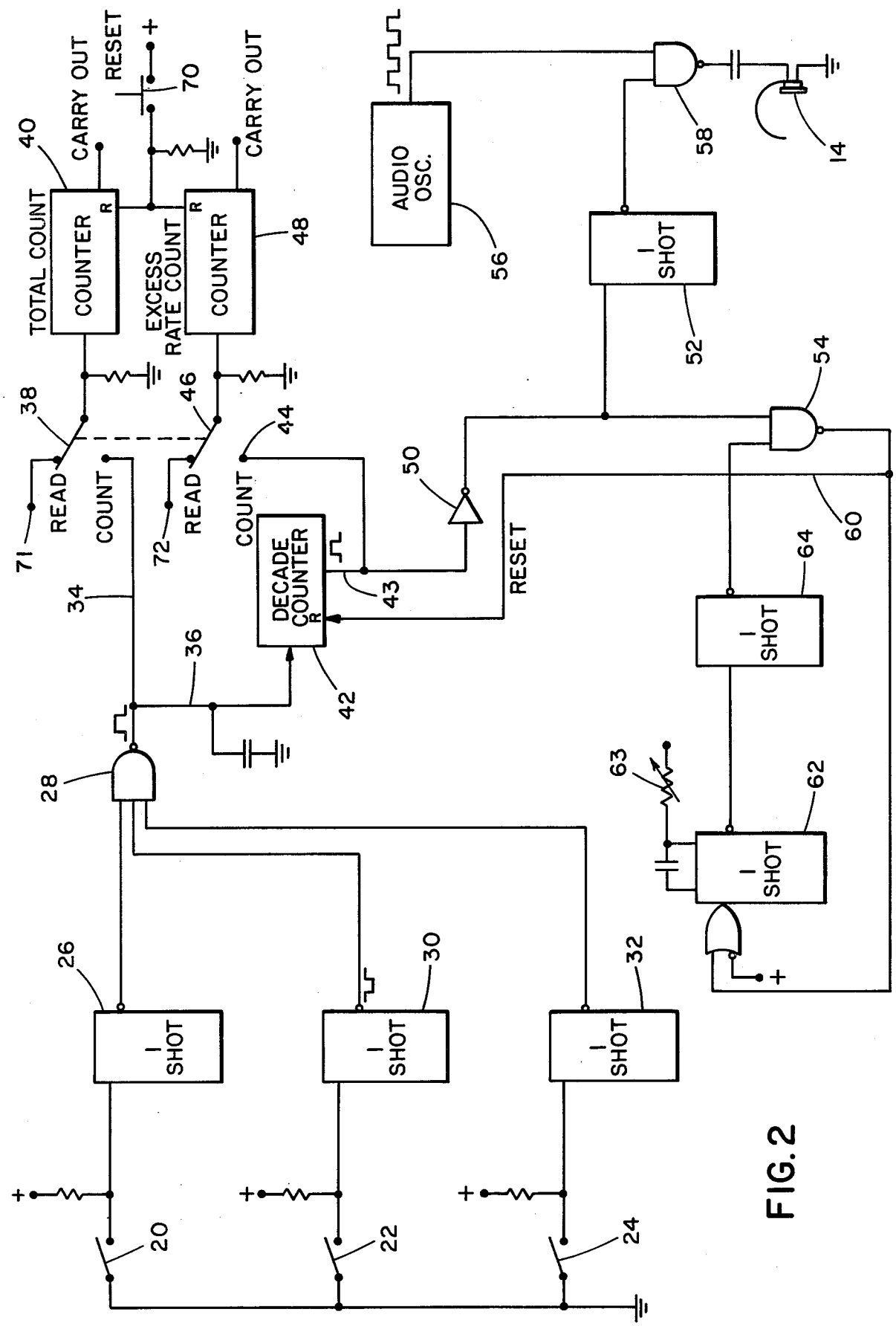
FIG. 2 is a schematic circuit diagram of the activity unit according to the invention.

Referring to FIG. 2, the schematic circuit of the activity unit 12 is illustrated. The activity unit 12 is a small box attached to a belt worn by the subject. The electronic circuit has three functions. First, to record the total number of activity counts; second, to record the total number of times the activity count exceeds a selected maximum during a selected time interval (hyperactivity); and third, to provide an audible feedback signal through the earphone when hyperactivity is detected.

When the count stored in the activity unit 12 is to be read out the unit is connected by a cable 16 to a readout and display unit 18. Since the activity unit 12 is capable of counting and storing a record of the subject's activity over a period of time, constant monitoring is not necessary. It is possible to have the subject visit the physician's office periodically to have the activity information read out.

Activity of the subject is detected by means of three mercury type microswitches 20, 22 and 24. These switches are mounted in a plane parallel to the ground when the box is worn at the waist. The switches are physically oriented at 120° to each other so that movement in any direction at the waist will displace the mercury in at least one of the switches thereby opening the contact. Of course, a greater or fewer number of such switches could be employed depending upon the application.

Opening any one of switches 20, 22 and 24 represents an activity count for the purpose of determining the total activity of the subject. When switch 20 is opened it provides a positive voltage to one shot multivibrator 26 which produces a negative going pulse to NAND gate 28. Similarly, opening switch 22 produces a pulse from one shot 30 and opening switch 24 produces a pulse from one shot 32. The inputs to NAND gate 28 are normally high causing a low output therefrom. When any of the one shots produce a negative pulse the output of NAND gate 28 goes high producing a pulse on lines 34 and 36.

When the device is in the counting mode, line 34 is connected by a switch 38 to a binary counter 40. Binary counter 40 may be of a commercially available type as, for example, an MC 14020 CP. Each time one of the microswitches is opened a count is registered and stored in counter 40.

Via line 36 the count signal is also provided to a decade counter 42. A selected output from the decade counter is provided to terminal 44. In the count mode a switch 46, ganged to switch 38, provides a count from the decade counter to a second binary counter 48. Counter 48 may be identical to counter 40. The output of the decade counter is also provided via inverter 50 to a one shot 52 and NAND gate 54. One shot 52, when activated by the output from the decade counter, will gate audio oscillator 56 through the NAND gate 58 to the earphone 14.

The output applied to NAND gate 54 is effective for resetting the decade counter via line 60 and variable delay one shot 62. The output of the variable delay one shot 62 is connected to a one shot 64 which, in turn, is provided as the second input to the NAND gate 54. The decade counter 42, gate 54 and one shots 62 and 64 comprise the excess rate determining circuit. When an excess rate is detected, a count is stored in excess rate counter 48.

One shots 62 and 64 set the period against which the number of counts received are compared. By adjusting the resistor 63 the delay period of one shot 62 can be changed to produce a selected timing interval appropriate for the specific subject being monitored. Typically, a period on the order of ten seconds is satisfactory. At the termination of that period a negative going pulse from one shot 64 is applied to NAND gate 54 effective for resetting the decade counter 42 and re-triggering the one shot 62 to start a new time period. Thus, if no counts are received by the decade counter 42, it will be periodically reset by the output of the one shot 64.

Decade counter 42 has a plurality of outputs, one for each of ten counts. If, for example, the output corresponding to a three count is selected, an output on line 43 will be produced when the counter reaches three if it is not first reset by the one shot 64. As stated, the output from counter 42, if produced, is applied to NAND gate 54. Thus, either the one shot 64 or the decade counter 42 will operate gate 54 to reset the counter and re-trigger the one shot 62. If fewer than three counts are received during a timing interval, one shot 64 will reset the decade counter. The decade counter will, therefore, not produce an output to counter 48.

Alternatively, if three or more counts are received by the decade counter before the end of the timing interval, the output from the decade counter will operate gate 54 and provide a count to the excess rate counter 48. In this manner counter 48 contains a count of the number of times the subject's activity count per unit time exceeds a selected threshold.

Where it is desirable to condition the subject not to exceed a selected activity rate the biofeedback portion of the circuit is employed. The audio oscillator 56 produces a tone in the frequency range detectable by the human ear. The oscillator tone is gated to the earphone 14 by the one shot 52. Thus, each time the decade counter detects an excess number of counts per unit time it triggers the one shot 52 sending a tone burst to the earphone 14 or other indicating device.

Periodically, the activity unit counters must be read out to determine the total count and the excess rate count. This is accomplished by connecting counters 40 and 48 to the circuit of FIG. 3. This is accomplished by moving switches 38 and 46 from the count position to the read position. This disconnects them from the mercury switches and prevents false counts from being entered. After readout has been accomplished, the counters 40 and 48 are reset by operating pushbutton 70. As will be readily appreciated, the entire circuit, since it is contained in a small box affixed to the belt of the subject, is battery powered.

Figure 3:
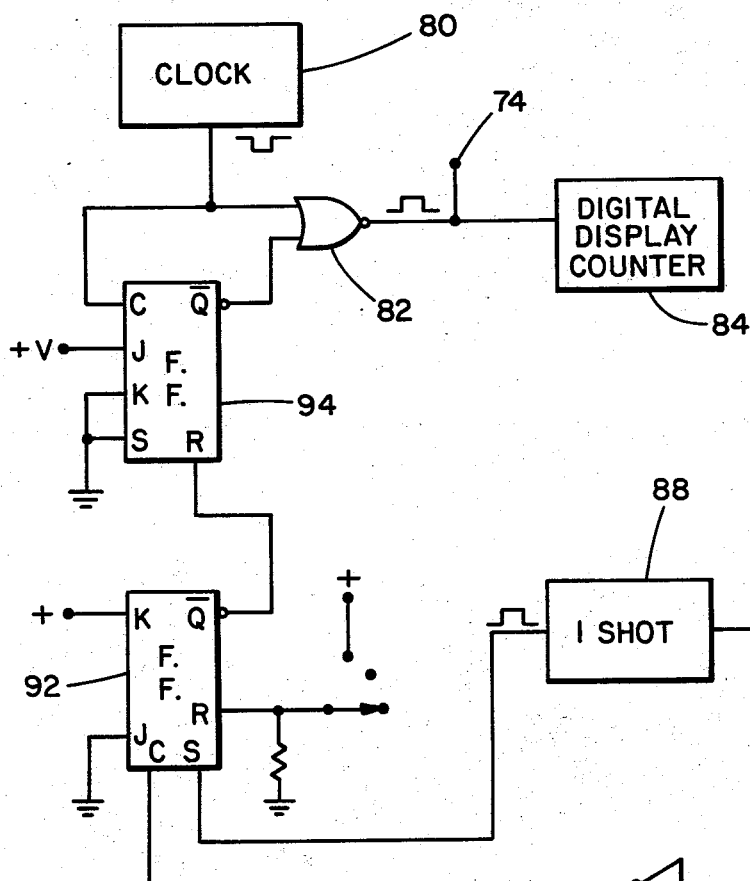
FIG. 3 is a schematic diagram of the readout unit according to the invention.

In order to read out the contents of counter 40, terminal 71 is connected by terminal 74 of the FIG. 3 circuit by a cable. Counter 48 is read out in a similar manner connecting terminal 72 to terminal 74. The particular counter being read out has its carry output connected to terminal 76. The FIG. 3 circuit provides counts to the counter until the counter overflows and the carry out signal is produced stopping the counts.

A clock 80 produces a series of pulses gated by NOR gate 82. The output of NOR gate 82 is provided to one of the counters 40, 48, via terminal 74 and to a display readout device 84. Exemplary of such a display device is the Fluke Model 1900A Multicounter. The clock provides pulses to the counter until overflow is detected. These pulses are counted by the display device 84. Since the capacity of the counters 40 and 48 is known, the number of counts stored therein can be determined by substracting the reading on the display device 84 from the counter capacity.

Readout is controlled by a pushbutton 86. When the button is depressed a one shot 88 produces a pulse via switch debounce circuit 90 effective for setting a JK flipflop 92. Setting flipflop 92 causes the Q-NOT output to go low. This output is connected to the reset input of flipflop 94. The Q-NOT output of flipflop 94 then goes low permitting clock pulses from clock 80 to pass the NOR gate 82. When the counter overflows, the carry out provided at terminal 76 clears flipflop 92 and, accordingly, the Q-NOT output goes high. In turn, flipflop 94 is reset and clock 80 no longer can provide counts to the counters or the display device 84.

In order to determine the number of counts in a counter, it is only necessary to subtract the number shown on the display 84 from the counter capacity. This operation is performed for each of the counters 40 and 48 to determine the total count and the excess rate count. After the readings have been obtained the reset switch 70 is operated to clear the counters and the device may be returned to the subject for further use.

Embodiments of this invention have been shown and described in some detail. It will be understood, however, that this description and the illustrations are offered merely by way of example, and that the invention is to be limited in scope only by the appended claims.

We claim:

1. A method of measuring hyperactivity in a human being comprising the steps of:
   (a) detecting physical movement of said human;
   (b) incrementing a first counting means each time physical movement is detected;
   (c) repetitively generating a timing interval;
   (d) determining when the number of physical movements during said timing interval exceed a selected maximum thereby indicating hyperactivity;
   (e) incrementing a second counting means and initiating a new timing interval each time the selected maximum is exceeded;
   (f) periodically reading out the values stored in the first and second counting means,
   whereby the degree of hyperactive behavior may be determined.

2. The method of claim 1 further including the step of providing biofeedback to said human each time said selected maximum is exceeded to inform the human that his activity rate exceeds said selected maximum.

3. The method of claim 2 wherein the biofeedback provided is aural.

4. The method of claim 2 wherein the biofeedback provided is visual.

5. The method of claim 1 wherein said step of detecting includes the substeps of:
   (a) locating at least one movement activated switch on the person of said human;
   (b) producing an electrical pulse indicative of movement each time said switch is activated.

6. The method of claim 1 wherein step (d) includes the substeps of:
   (a) incrementing a third counting means each time physical movement is detected during said timing interval;
   (b) producing an electrical signal when the count in said third counting means exceeds said selected maximum;
   (c) resetting said third counting means to zero at the end of said timing interval or when said electrical signal is produced, whichever first occurs,
   said second counting means being incremented each time said electrical signal is produced by said third counting means.

7. A device for measuring hyperactivity in a human being comprising:
   (a) means for detecting physical movement of said human;
   (b) first counting means incremented each time physical movement is detected;
   (c) means for repetitively generating a timing interval;
   (d) second counting means;
   (e) determining means for incrementing said second counting means and initiating a new timing interval when the number of physical movements during a preceding timing interval exceed a selected maximum; and
   (f) means for periodically reading out the values stored in said first and second counting means.

8. The device according to claim 7 further including means for providing biofeedback to said human each time said selected maximum is exceeded to inform the human that his activity exceeds said selected maximum.

9. The device according to claim 8 wherein said biofeedback means includes an audio oscillator, an earphone for use by said human, and means for gating said audio oscillator to said earphone each time said selected maximum is exceeded.

10. The device according to claim 7 wherein the means for detecting includes switch means for location on the person of said human and means for producing an electrical pulse indicative of movement each time said switch means is activated, said determining means and first counting means being responsive to said electrical pulse.

11. The device according to claim 10 wherein said switch means comprise at least one mercury wetted switch provided in a plane parallel to the ground when worn at the waist of a human being.

12. The device according to claim 7 wherein said means for generating a timing interval includes a one shot multivibrator having a variable resistance element whereby the selection of the resistance value determines the length of said timing interval.

13. The device according to claim 7 wherein the means for determining includes:
   (a) a third counting means incremented each time physical movement is detected during said timing interval, said third counting means producing an electrical signal when the count therein exceeds said selected maximum;
   (b) means for resetting said third counting means to zero at the end of said timing interval or when said electrical signal is produced, whichever first occurs,
   said second counting means being incremented each time said electrical signal is produced by said third counting means.

14. The device according to claim 7 wherein the means for periodically reading includes:
   (a) means for generating pulses;
   (b) a display counter;
   (c) means for applying said pulses to one of said first and second counting means and to said display counter;
   (d) means for terminating the application of pulses to said one of said first and second counting means and said display counter on detecting overflow from said one counter,
   whereby the content of said one of said first and second counting means is determined by subtracting the number of pulses registered by said display counter from said one counter's capacity.

* * * * *